(12) United States Patent
Grace

(10) Patent No.: US 6,188,470 B1
(45) Date of Patent: Feb. 13, 2001

(54) BIOENERGETIC DATA COLLECTION APPARATUS

(75) Inventor: Robert John Grace, Prospect (AU)

(73) Assignee: Larkace Pty Ltd, Nailsworth (AU)

(*) Notice: Under 35 U.S.C. 154(b), the term of this patent shall be extended for 0 days.

(21) Appl. No.: 09/331,993

(22) PCT Filed: Dec. 30, 1996

(86) PCT No.: PCT/AU96/00841

§ 371 Date: Jun. 30, 1999

§ 102(e) Date: Jun. 30, 1999

(87) PCT Pub. No.: WO97/24980

PCT Pub. Date: Jul. 17, 1997

(30) Foreign Application Priority Data

Jan. 4, 1996 (AU) .................................................. PN7407

(51) Int. Cl.⁷ .................................................. G01N 33/48
(52) U.S. Cl. .............................. 356/39; 356/42; 600/556; 600/336
(58) Field of Search ................................. 356/39, 41, 42; 600/556, 523, 323, 13–15, 333–336, 326, 477, 478

(56) References Cited

U.S. PATENT DOCUMENTS

| | | |
|---|---|---|
| 4,773,422 | 9/1988 | Isaacson et al. . |
| 4,819,657 | * 4/1989 | Kraft et al. .......................... 600/556 |
| 4,846,183 | * 7/1989 | Martin .................... 356/41 |
| 5,246,002 | 9/1993 | Prosser . |
| 5,323,776 | 6/1994 | Blakeley et al. . |
| 5,408,998 | 4/1995 | Mersch . |
| 5,527,259 | 6/1996 | Grace et al. . |
| 5,560,355 | * 10/1996 | Merchant et al. ..................... 356/41 |
| 5,588,425 | * 12/1996 | Sackner et al. ...................... 600/523 |

FOREIGN PATENT DOCUMENTS

| | | |
|---|---|---|
| 33187/71 | 9/1970 | (AU) . |
| 60745/80 | 10/1981 | (AU) . |
| 75189/91 | 3/1982 | (AU) . |
| 11537/95 | 8/1995 | (AU) . |
| 12063/88 | 9/1998 | (AU) . |
| 286142 | 10/1988 | (EP) . |
| 335356 | 10/1989 | (EP) . |
| WO 88/01149 | 2/1988 | (WO) . |
| WO 90/09146 | 8/1990 | (WO) . |
| WO 91/13589 | 9/1991 | (WO) . |
| WO 92/21283 | 12/1992 | (WO) . |
| WO 94/27492 | 12/1994 | (WO) . |
| WO 94/27493 | 12/1994 | (WO) . |
| WO 95/16388 | 6/1995 | (WO) . |

OTHER PUBLICATIONS

Remington; "A History of Electrodermal Testing"; pp. 3–20, Jul. 1990.
Derwent Abstract accession No. H4483W/29, SU 438412, (Kuan Med Inst.), Jan. 30, 1975.
Derwent Abstract Accession No. J5112B/40, Class P31, SU 639525 (Lith Epidemol. Micro.), Feb. 26, 1979.

* cited by examiner

Primary Examiner—Frank G. Font
Assistant Examiner—Sang H. Nguyen
(74) Attorney, Agent, or Firm—Merchant & Gould P.C.

(57) ABSTRACT

A Bioenergetic Data Collection Apparatus utilizing a modified oximeter (1) to collect signals characteristic of blood flow in terminal tissue, such as a finger tip (12). A processing means (7) in signal connection with the modified oximeter (1) receives and analyzes the signals to produce pulse waveforms, or a pulse waveform sequence, that is displayed on a high resolution video display (5). An isolation means (8) is provided between the modified oximeter (1) and the processing means (7) to ensure no lethal voltages can threaten a patient. A variety of aids are provided to assist an appropriately skilled practitioner to make a prognosis from the displayed data. The tools include measurement of the ratio of heart activity to heart rest, variation in systolic pulse amplitude, variation in pulse shape, etc.

14 Claims, 14 Drawing Sheets

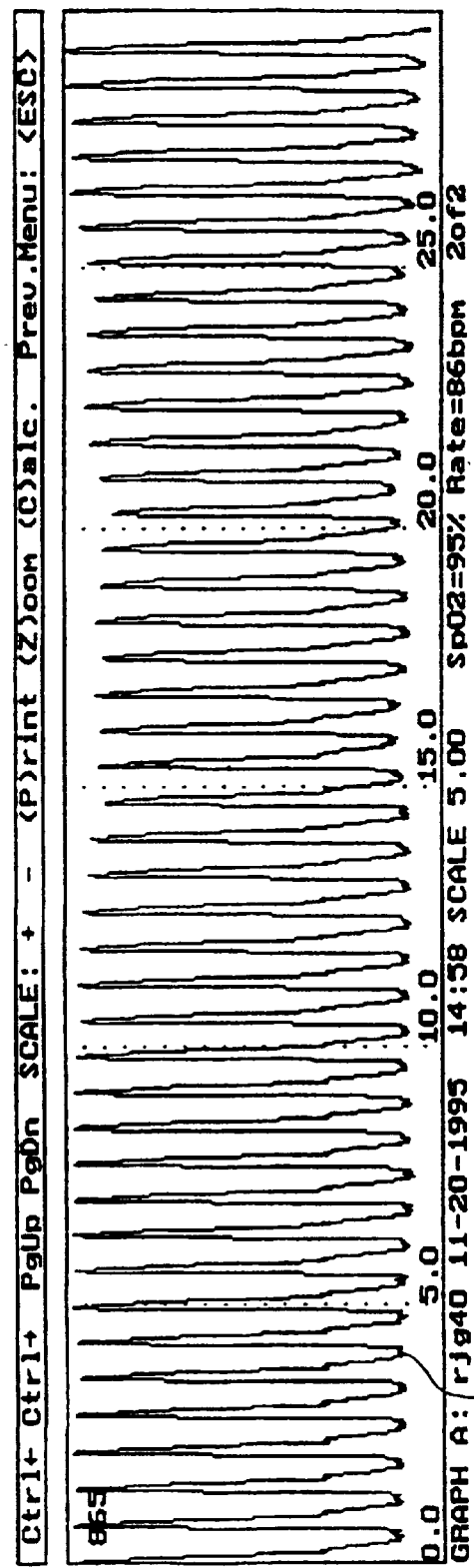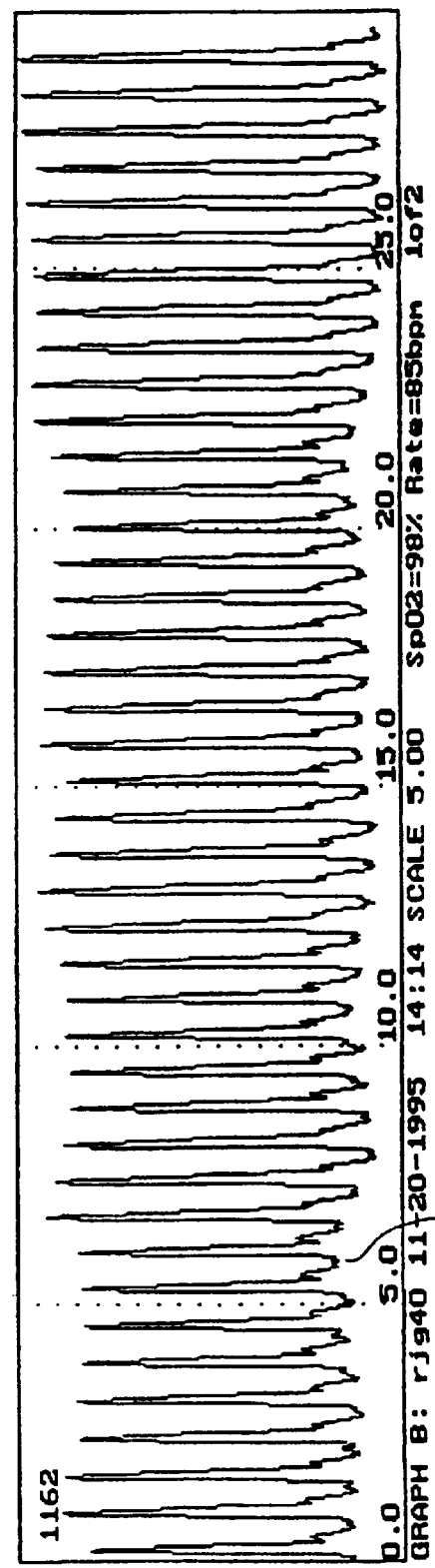
FIG. 9

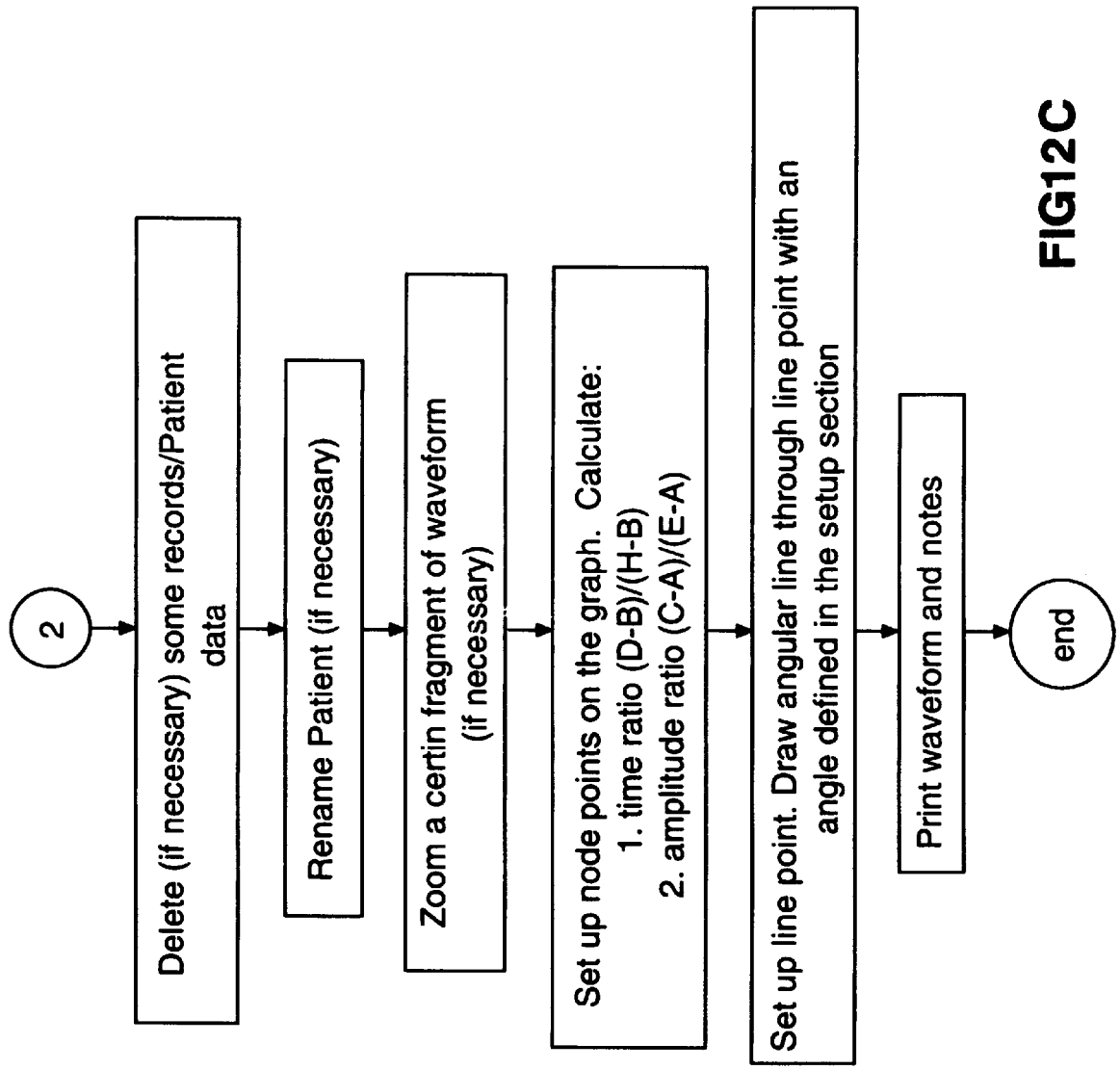

BIOENERGETIC DATA COLLECTION APPARATUS

FIELD OF THE INVENTION

This invention relates to a method and apparatus for the collection of biomedical data. In particular, it relates to a bioenergetic approach to the evaluation of observed cardiovascular response as recorded in terminal tissue, such as the fingertip. The invention finds primary application with humans but may also be applied to animals.

BACKGROUND TO THE INVENTION

Biomedical data can be collected using electronic instruments that utilize electromagnetic energy in various ways. A useful summary of known devices and techniques has been presented by Dr. Dennis W Remmington to the Joint Committee Meeting of the Utah State Medical Association and published in July 1990. He summarises the known devices in two categories: instruments which measure passive electrical energy, and instruments which measure response to stimuli.

The first category includes instruments such as the electrocardiograph (ECG). the electroencephalograph (EEG), Chinese electric pulse testing, and Chinese gastrointestinal analysis.

In the second category are instruments that measure response to stimuli, such as galvanic skin response devices, and instruments that measure response to electromagnetic stimuli, such as electromyelography, brain stem audiometry, magnetic resonance imaging (MRI) and electroacupuncture according to Voll (EAV).

The galvanic skin response technique measures the electrical conductance between two electrodes placed on the skin. The patient is then subjected to various stimuli, and any change in skin conductance is recorded. Any stimuli causing increased sweat production will Increase the conductance and give a change in the readings, which are usually recorded on a graph.

In the EAV method a low voltage electrical charge is Introduced into the body. and the precise level of electric current conducted through the acupuncture points are measured. Information about various organ systems and musculoskeletal regions is obtained by the level of the readings.

The known devices have proven useful to various degrees in providing biomedical data to assist medical practitioners in diagnosis. However, the majority of the known techniques are invasive and require the application of electric current to the patient. Furthermore, the known techniques are subjective in nature and subject to wide variation in interpretation of indicative measures. A method and apparatus for passively collecting bloenergetic data is desirable.

The collection of bioenergefic data, such as pulse rate, by monitoring of blood movement in the fingertip is known. Common devices for performing this function comprise a red or infrared light source and detector. The light incident on the fingertip penetrates a small distance into the fingertip and is modulated by absorption in the blood in the capillaries. A portion of the light is reflected or transmitted and this is measured by the detector. Thus the signal from the detector mimics the flow of blood through the fingertip.

These devices are not limited to use at the fingertip or with humans. Devices for use with animals commonly measure blood movement at the ear lobe, lip or tongue.

The majority of the applications of the device described above are for simple monitoring of pulse rate. In some applications, the signals from the device are analysed in more detail to separately identify the systolic and diastolic pulses.

In recent times the devices have become more sophisticated with the advent of more intense light sources and more sensitive detectors. It is now possible to estimate the partial pressure of oxygen in the body by monitoring absorption of infrared light In the blood and making a number of assumptions. Devices performing this function are generally known as oximeters.

The inventors have found that a great deal more information can be obtained by monitoring blood flow in the fingertip than has previously been realised.

OBJECT OF THE INVENTION

It is an object of the present invention to provide an apparatus for the monitoring and evaluation of observed cardiovascular response.

A further object of the present invention is to provide a method of monitoring and evaluating cardiovascular response.

Further objects will be evident from the following description.

DISCLOSURE OF THE INVENTION

In one form, although it need not be the only or indeed the broadest form, the invention resides in an apparatus for the collection of bioenergetic data comprising:

monitoring means adapted to produce signals characteristic of blood flow;

processing means in signal connection with said monitoring means and adapted to receive and analyse said signals to indicate the bioenergetic status of a body; and display means adapted to display the bioenergetic status so indicated.

In preference the apparatus further comprises an isolation means in signal connection with the monitor means and processing means. The isolation means preferably provides electrical isolation between the monitoring means and the processing means so as to ensure that the relatively high voltages in the processing means cannot be transmitted to a patient through the monitoring means.

In preference the monitoring means comprises an oximeter adapted to monitor blood flow in an extremity, such as a fingertip or ear lobe. The oximeter preferably comprises a light source, detector means and interface means. The detector is preferably a photodiode. The light source may be a light emitting diode (LED) or diode laser emitting infrared or visible radiation. Preferably, there are two light sources, one emitting infrared radiation and one emitting visible radiation. The signals from the detector are indicative of the nature of the blood flow in the extremity. The interface means performs preliminary processing of the signals from the detector including converting the analogue detector signals to digital signals suitable for the processing means.

In preference the processing means is a microprocessor programmed to measure characteristics of the received signals. The measured characteristics Include such characteristics as:

the ratio of heart activity to heart rest the variation in systolic pulse amplitude over time the ratio of systolic pulse amplitude to diastolic amplitude variation in shape from pulse to pulse variation in pulse shape over time.

In preference the bioenergetic status of the body is indicated according to such functions as:

pulse rate oxygen saturation in terminal tissue ($SpO_2$)

blood flow rate elasticity of blood vessels strength and regularity of the heart beat cardiac sufficiency cardiac valve activity cardiac or vascular metabolic abnormalities cell energy change latent hypertension myocardium damage cardiac or vascular inflammation allergic reactions immune system response changes pulmonary/cardiac function variations bioenergetic reactions at lining of intestine The display means is suitably a high resolution video display adapted to display graphical and alphanumeric data. The graphical data preferably includes a representation of the measured pulse shape or a series of measured pulses. The alphanumeric data preferably includes indications of one or more of the above characteristics or functions.

In preference, the apparatus further comprises memory means in signal connection with the processing means. The memory means may provide transient storage of data, permanent storage of data or both.

The apparatus may further comprise an EKG module to provide an electrical readout of the heart function for an objective profile of the cardiac function, an allergy module for providing an objective computer based evaluation and assessment of electrodermal readings of known allergens by registering before and after microvoltage changes in response to allergens, and a pulse blood pressure module for providing diastolic, systolic and mean arterial pressure.

In a further form the invention resides in a method of collecting bioenergetic data of a body including the steps of:

transmitting visible and infrared radiation into terminal tissue;

measuring a voltage signal proportional to visible and infrared radiation transmitted through the terminal tissue;

converting the voltage signal to a digital signal;

passing the digital signal to a processing means;

processing the digital signal in the processing means to produce a displayable waveform; and displaying the displayable waveform on a display means.

The method may include the further steps of analysing the waveforms to provide indicative measures of the cardiovascular health of the body.

BRIEF DETAILS OF THE DRAWINGS

To further assist in understanding the invention reference will be made to the following drawings in which:

FIG. 9 shows a comparison of a waveform for a patent before and after exposure to a therapeutic magnetic field;

DETAILED DESCRIPTION OF THE DRAWINGS

Figure 1:
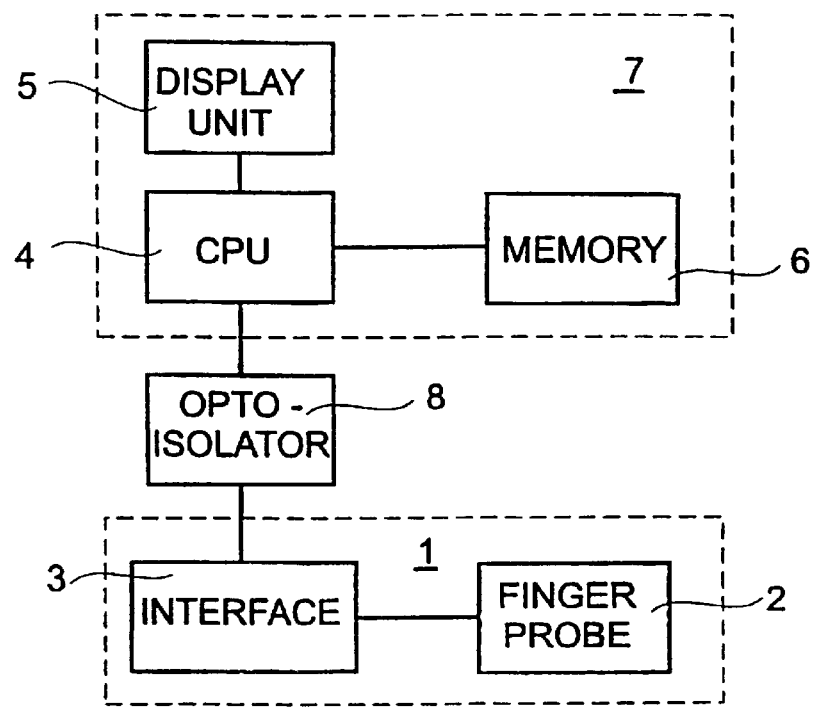
FIG. 1 is a block diagram of the components of an apparatus for collection of Bioenergetic data.

In the drawings, like reference numerals refer to like parts.

Referring now to the drawings in detail there is shown in FIG. 1 a block diagram of a bioenergetic data collection apparatus according to a first embodiment. The apparatus comprises a monitor means 1, which in the preferred embodiment is an oximeter comprising a finger probe 2 and interface 3. Signal processing is performed in processing means 4. Associated with the processing means 4 is a display unit 5 and memory 6. In the preferred embodiment the processing means 4, display unit 5 and memory 6 together comprise a personal computer 7. The personal computer 7 may conveniently be a laptop computer thereby making the whole apparatus portable.

The interface 3 is in signal connection with an isolation means, such as opto-isolator 8, which is in signal connection with the processing means 4. The interface 3 has its own power supply so the only requirement for connection between the oximeter 3 and personal computer 7 is for the transmittal of signals from the interface 3 to the computer 7 via the opto-isolater 8. The opto-isolator 8 primarily provides electrical isolation between the interface 3 and the processing means 4 to avoid any risk of electrical injury to persons using the apparatus.

Figure 2:
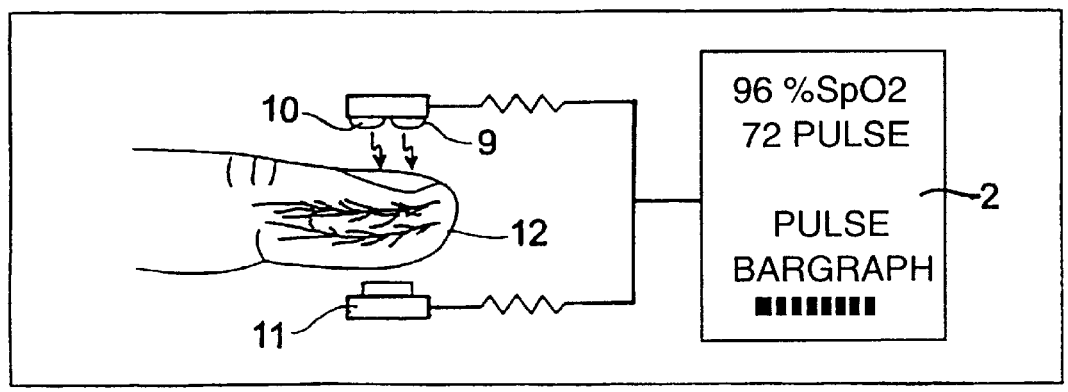
FIG. 2 is a detailed sketch of an oximeter.

The operation of the pulse monitor and finger probe are shown in more detail in FIG. 2. A commercially available device such as a model 71000A2 pulse oximeter from BCI International may be modified for use in the bioenergetic data collection apparatus. The finger probe comprises an infrared light source 9, a red light source 10 and a detector 11. In normal operation the oximeter determines $SpO_2$ and pulse rate by passing two wavelengths of light, one red and one infrared, through body tissue 12 to the photodetector 11. The light sources are pulsed and the photodetector signal is sampled at 120 Hz. During measurement, the signal strength resulting from each light source depends on the colour and thickness of the body tissue, the probe placement, the intensity of the light sources, and the absorption of the arterial and venous blood (including the time varying effects of the pulse) in the body tissues.

The oximeter processes these signals, separating the time invariant parameters (tissue thickness, skin colour, light intensity, and venous blood) from the time variant parameters (arterial volume and $pO_2$) to identify the pulse rate and calculate oxygen saturation. Oxygen saturation calculations can be performed because oxygen saturated blood predictably absorbs less red light than oxygen depleted blood.

The signal from the interface 3 is a time varying voltage with fast amplitude changes. The processing means 4 requires signals in a digital form so the interface 3 is required to sample and digitise the signal from the probe 2. Prior art devices have applied a relatively course digitising filter which has resulted in the loss of information rich high frequency components of the signal.

The commercially available oximeter requires two primary modifications for use in the bioenergetic data collection apparatus. Firstly, the output port of the interface 3 is adapted for connection to a standard serial port of a personal computer. Secondly, the bandpass of the interface 3 is modified to allow high frequency components to be transmitted to the processing means. Commercial devices routinely include a band-pass fiber to remove high frequency components and thereby obtain a more stable reading of the relatively low frequency pulse rate and $SpO_2$ values. The interface 3 provides a local readout of pulse and $SpO_2$.

The inventor has found it useful to filter out very low frequency signals that are caused by movement of the patient. Although the filtering can be performed in hardware by modification of the oximeter it is convenient to provide software filtering in the processing means.

Figure 3:
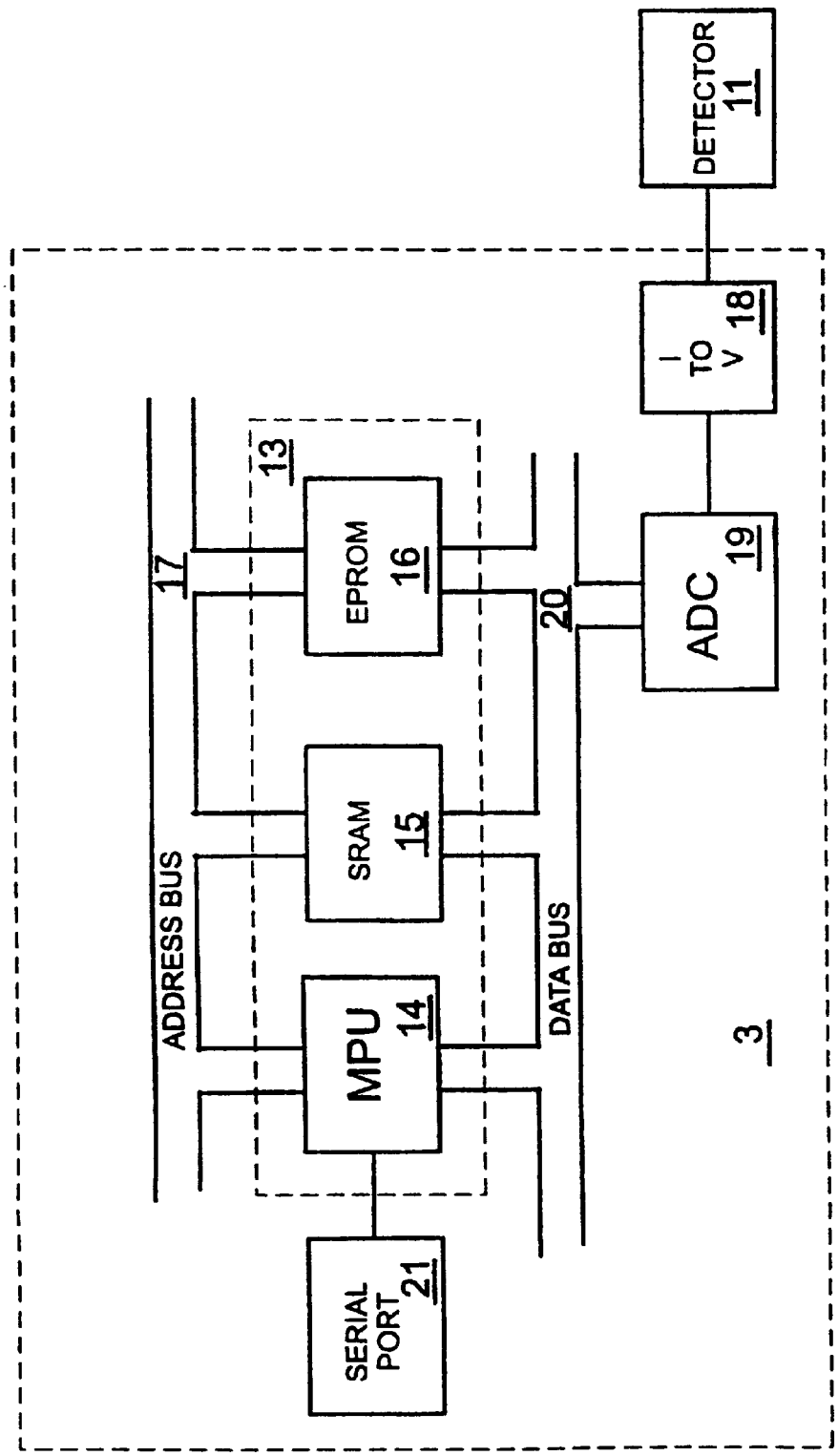
FIG. 3 is a schematic block diagram of the interface of the apparatus.

A schematic block diagram of the Interface 3 is shown in FIG. 3. A standard microprocessor kernel 13 is formed by microprocessor 14, RAM 15 and EPROM 16. Communication is provided on address bus 17. A current to voltage converter 18 converts the current output of the detector 11 to a voltage readable by the analogue to digital converter 19. The analogue to digital converter 19 performs a 12-bit conversion and places the digital result on data bus 20. The microprocessor 14 analyses the data to provide the local display and outputs the digital data through serial port 21.

The processing means 4 may be a personal computer programmed to analyze the signals received from the Interface 3. The personal computer may conveniently be a laptop computer which facilitates mobility of the apparatus. In the described embodiment the display means 5 is included as the monitor of the personal computer or laptop computer. In an alternative embodiment a purpose built processing means may be packaged into a compact container.

Figure 4:
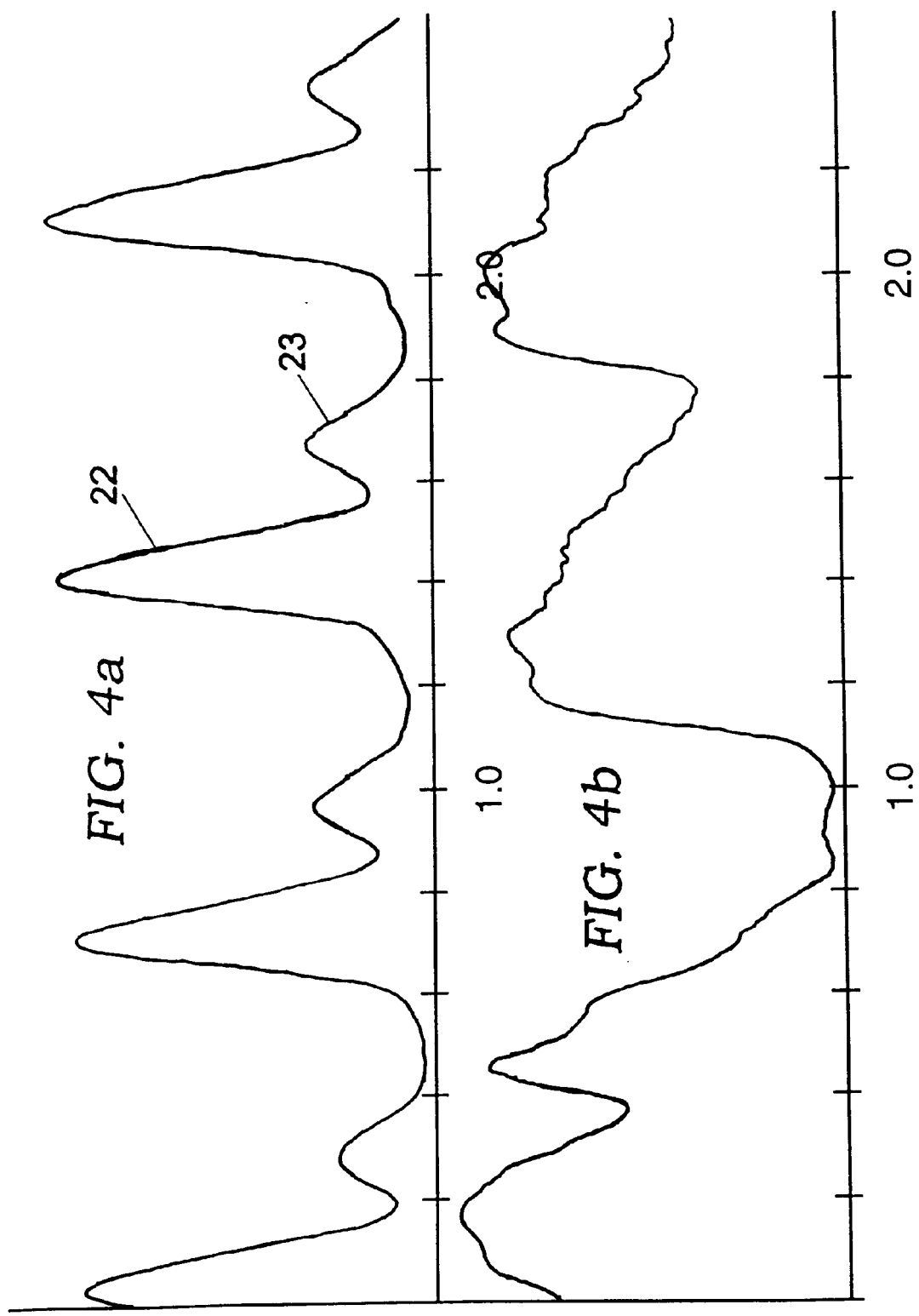
FIG. 4 shows a comparison of the waveform of a healthy person with a not so healthy person.

The apparatus may be operated in two main modes. In a first mode the apparatus monitors and collects data on the pulse of a subject. In this mode the apparatus is able to provide data in a form that facilitates diagnosis by a skilled medical practitioner. An example of the graphical data obtainable in this mode is given in FIG. 4. FIG. 4a shows a pulse trace recorded for a 20 year old male in good physical condition. The systolic 22 and diastolic 23 pulses are well defined and clean. In contrast, FIG. 4b shows a pulse trace for an individual in poor physical condition. The systolic and diastolic traces are poorly defined and very irregular. This trace indicates serious vascular problems.

Figure 5:
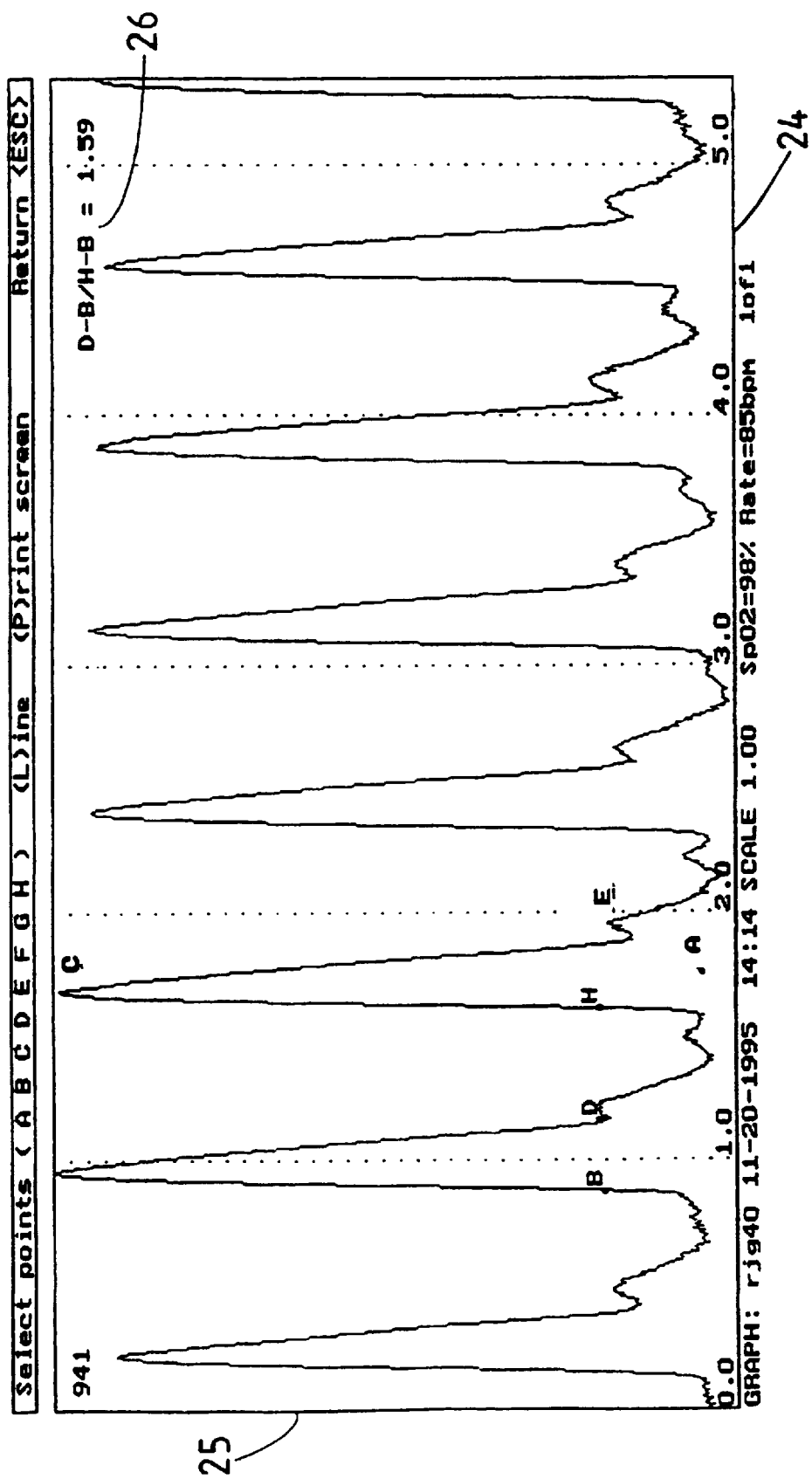
FIG. 5 is a trace showing the heart activity and amplitude ratio measurements.

Further analysis can be conducted on the recorded traces. FIG. 5 is a screen dump of a display demonstrating the calculation of heart activity. The X-axis 24 is marked in seconds and the Y-axis 25 is in arbitrary units. Identifying information including the date, file number, scale, $SpO_2$ and pulse rate are printed below the X-axis.

Heart activity is defined as the ratio of heart action to heart rest, which in the figure is calculated by D-B/H-B. The result of the calculation is shown on the screen at 26. The value provides useful information to a physician to aid in diagnosis. An amplitude ratio can also be calculated. The amplitude ratio is defined as C-A/E-A. The result may also be shown on screen.

Figure 6:
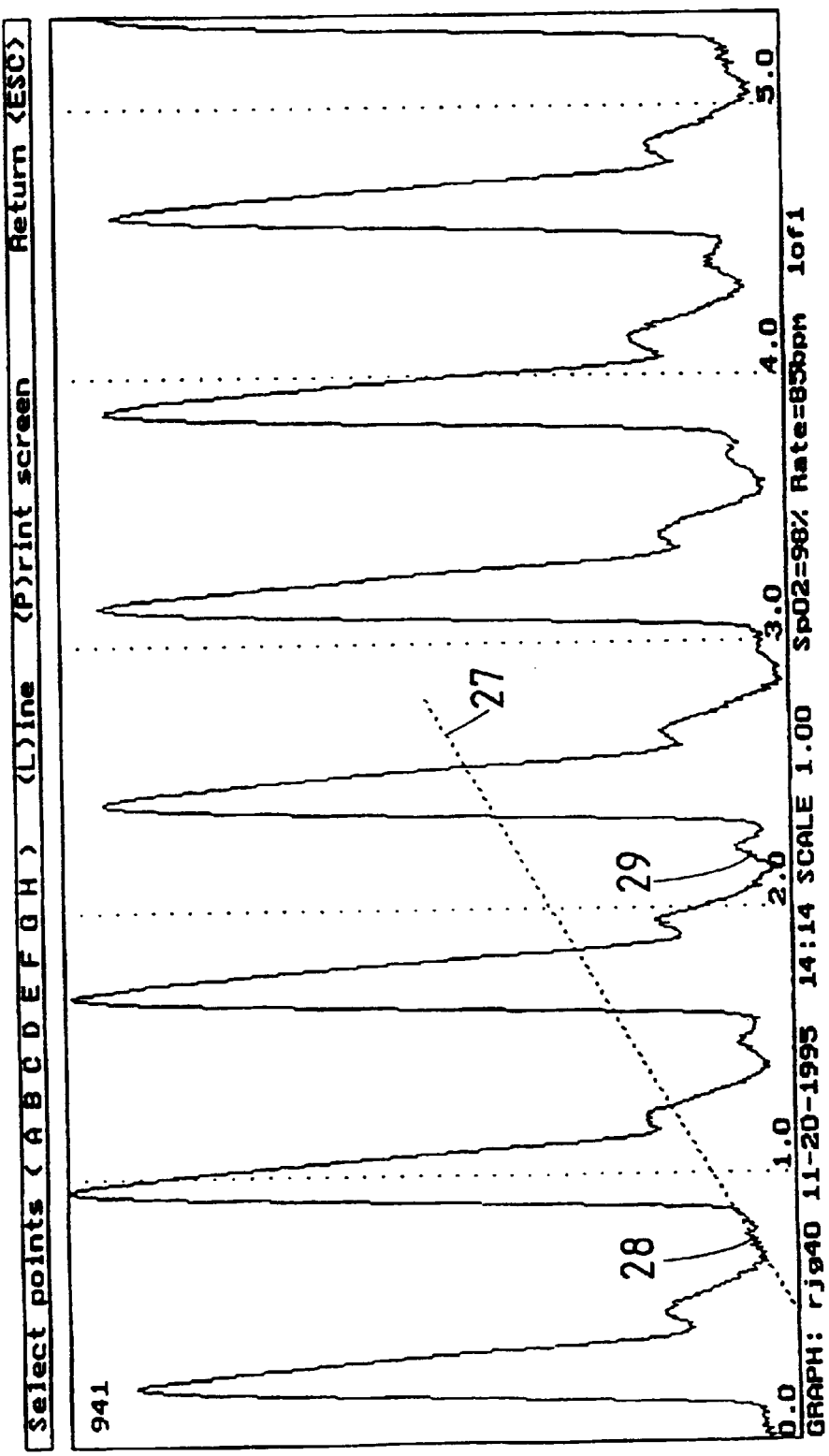
FIG. 6 is a trace showing an ATP ramp measurement.

FIG. 6 shows how the apparatus can be used to display and compare the ATP ramp angle. The angle of dotted line 27 can be set by the physician at the ATP ramp angle considered to be ideal for the patient and situation. The variation of a trace from the ideal angle is immediately evident In the example of FIG. 6 the region 28 Is good but the other regions, such as 29, deviate to a small degree. It will be appreciated that the example of FIG. 4b would show a marked deviation.

Figure 7:
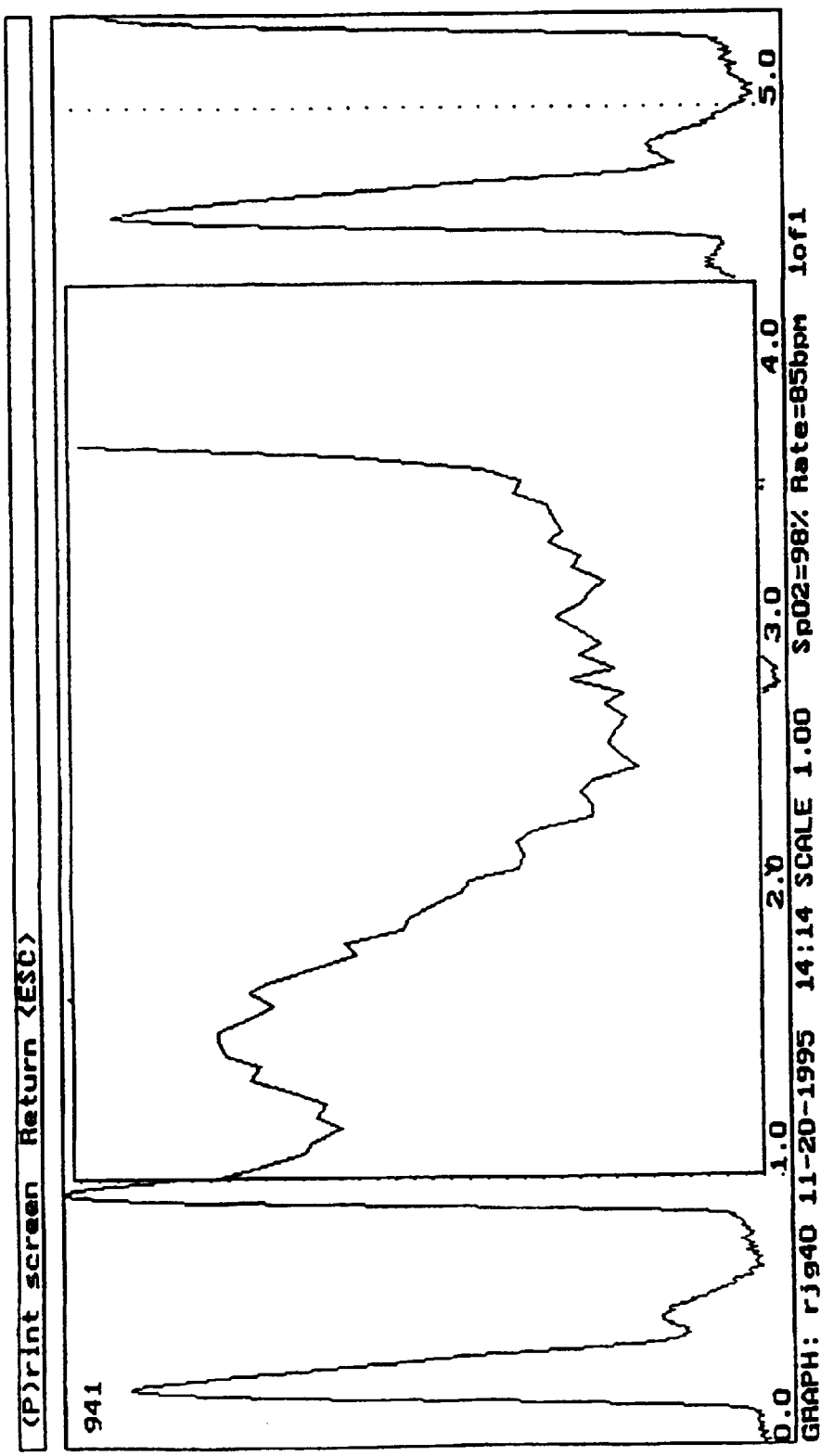
FIG. 7 is a trace showing an expansion of a modules notch region.

Regions of the pulse trace can be windowed and expanded as demonstrated in FIG. 7. In FIG. 7 the region around the dichotic notch has been expanded to show the high frequency components. It is generally accepted that this region of the pulse trace is indicative of gastrointestinal tract health. A bowel irritation may be manifest in an increase in high frequency components In this region. If every pulse in the trace shows a 'bump' in the ATP ramp region there Is likely to be a colon problem. If the 'bump' is intermittent, the problem is probably with ATP production (eg fatigue). The apparatus provides a display of this region to assist the physician to make a correct diagnosis.

Figure 8:
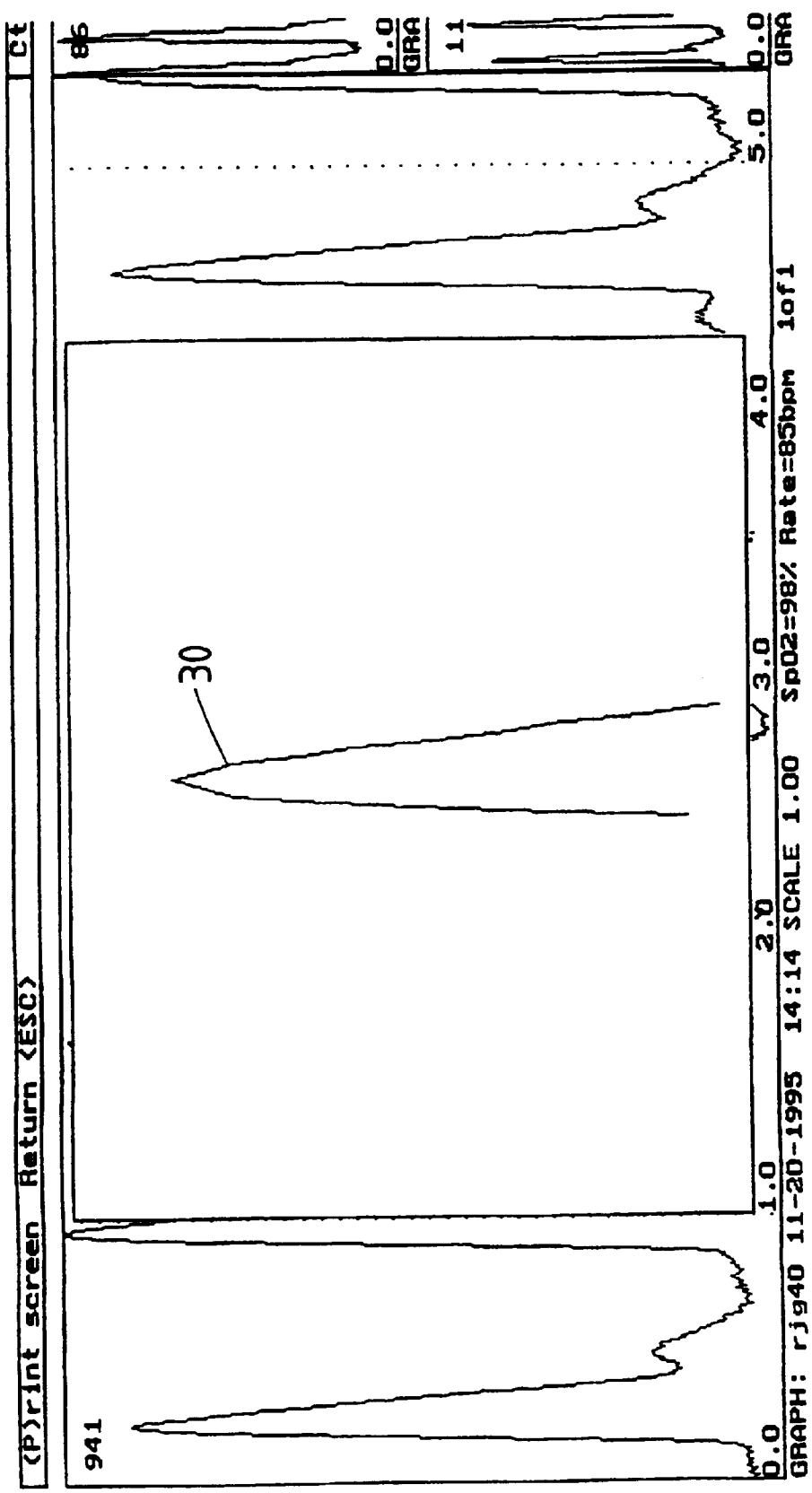
FIG. 8 is a trace showing an expansion of a systolic pulse.

In FIG. 8 the region around the top of the systolic pulse trace is enlarged. The shape of the trace in this region is generally accepted as indicative of the health of the aortic valve. A double peak is bad, whereas a single peak, such as 30, indicates good aortic valve condition. The physician can also obtain an estimate of the volumetric blood flow by measuring the height and width of the systolic pulse. This may also be used to diagnose overall heart condition.

In a second mode the data before a change can be stored in memory 6 and compared with data obtained after the change and an analysis provided. The change may be the application of a therapeutic magnetic field such as could be applied by the device described in U.S. Pat. No. 5,527,259. FIG. 9 indicates the differences that can be observed before and after the application of therapeutic magnetic fields.

In FIG. 9 the entire trace acquired over 30 seconds is shown. The lower trace, trace B, is the first acquired trace prior to application of a therapeutic magnetic field. The full trace is useful for showing pulse trends such as the variation in the pulse baseline 31. It Is clear in the lower trace that there is considerable variation in the baseline. In contrast the baseline 32 In the upper trace is relatively flat.

Figure 10:
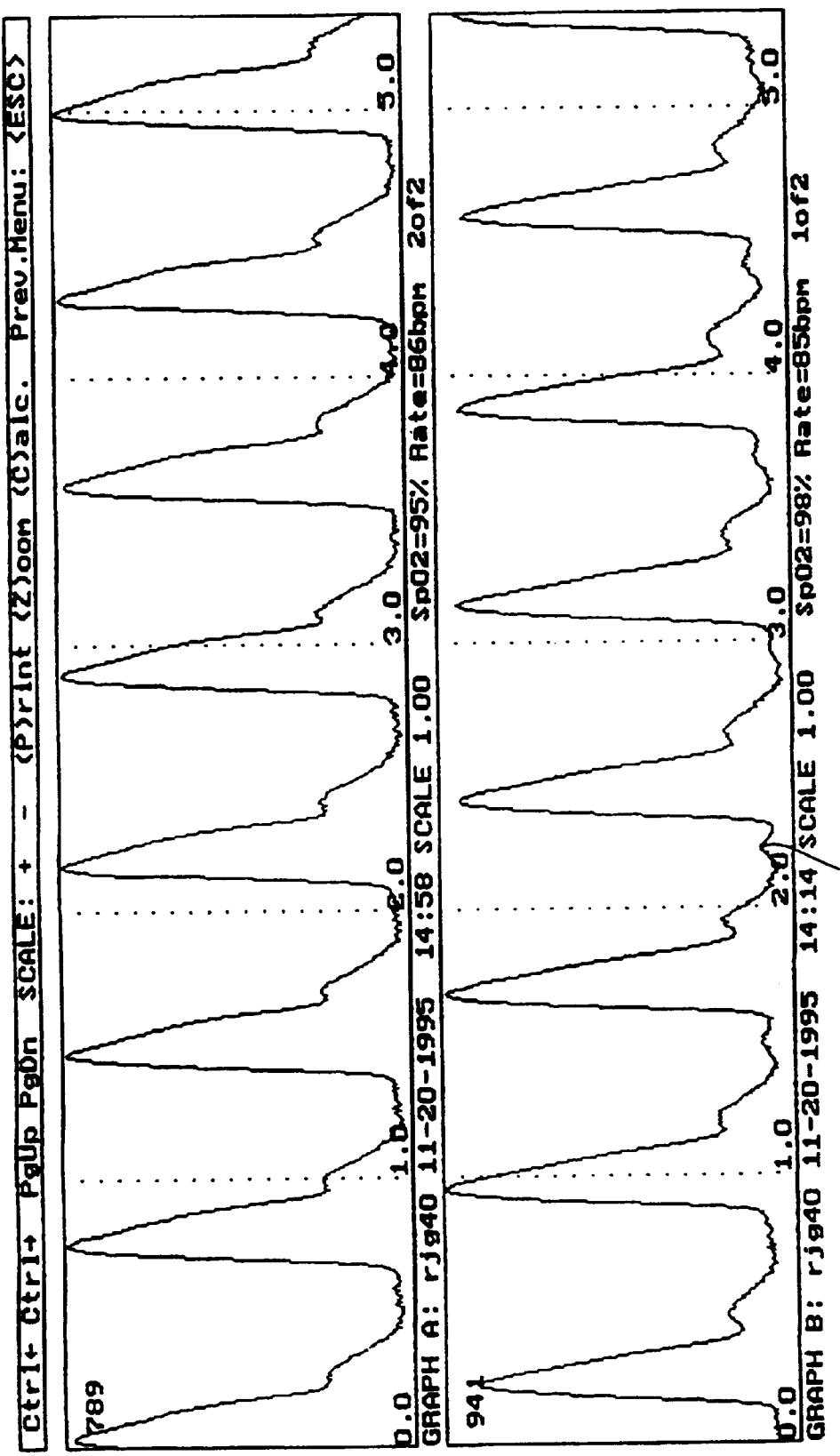
FIG. 10 is an expanded section of FIG. 9.

The scale can be expanded to highlight a subset of pulses. The first five seconds of the traces In FIG. 9 are shown in FIG. 10. This mode of display is useful for identifying changes in the pulse shapes as opposed to the pulse trends identified from FIG. 9. It is clear from FIG. 10 that the 'bumps' 33 evident in the ATP ramp of the lower trace are gone from the upper trace after application of therapeutic magnetic fields.

Figure 11:
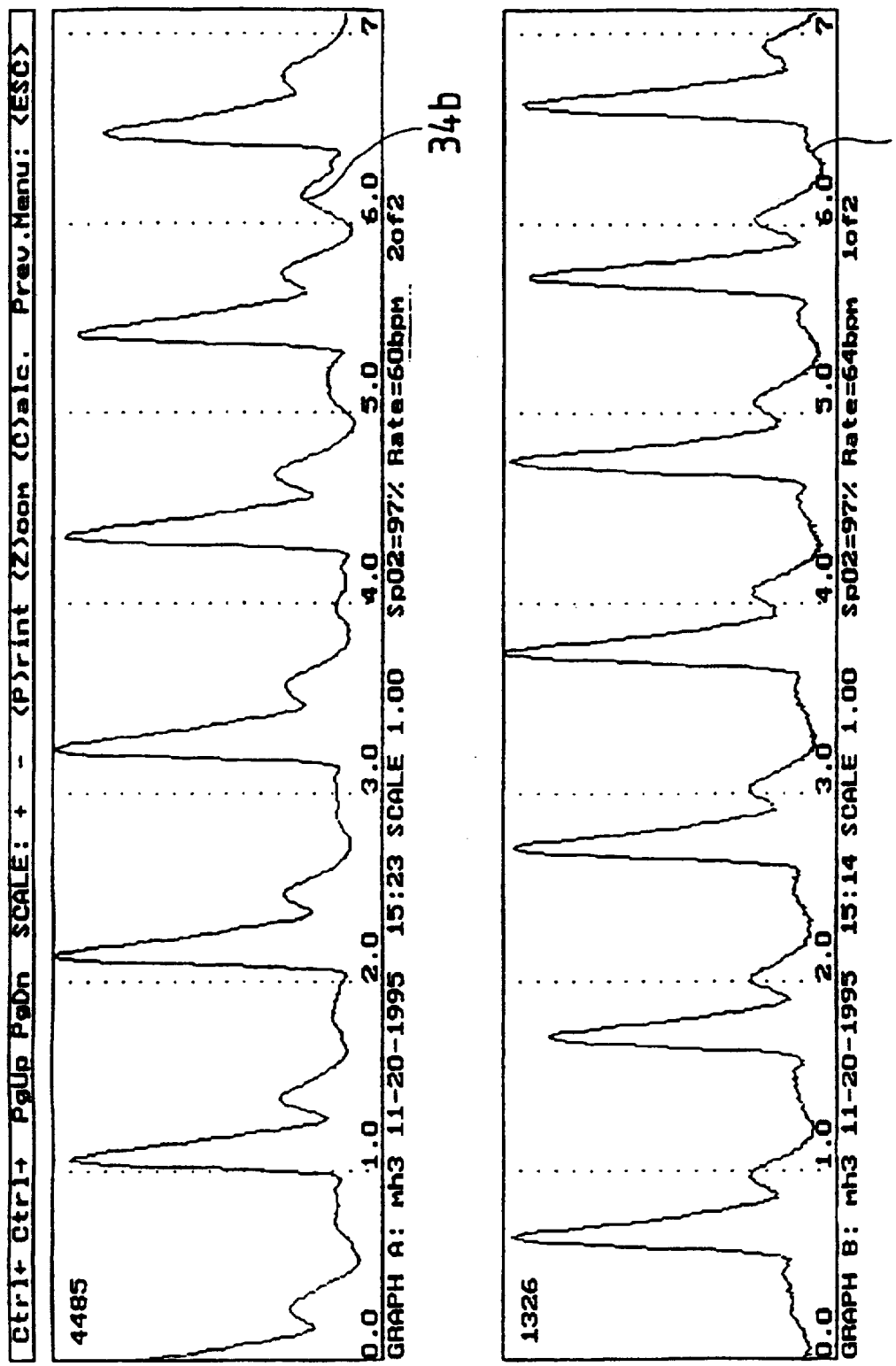
FIG. 11 is a comparison of a waveform for a patient before and after exposure to an allergen.

A comparison between traces can also be made to detect the impact of detrimental influences on the body. One such application is the identification of allergic response. FIG. 11 shows a comparison of traces taken without (lower trace) and with (upper trace) allergenic influence. The allergenic influence may be applied by a patient simply holding a vial containing allergenic materials. Kits of allergens can be obtained from homeopathic suppliers such as the Practitioner Test Kit obtainable from Brauer Biotherapies Pty Ltd. FIG. 11 dearly shows a disruption of the ATP ramp as indicated by 34a in the lowertrace and 34b in the upper trace. This disruption can be used by a physician to diagnose allergic reaction to different allergens.

Figure 12A:
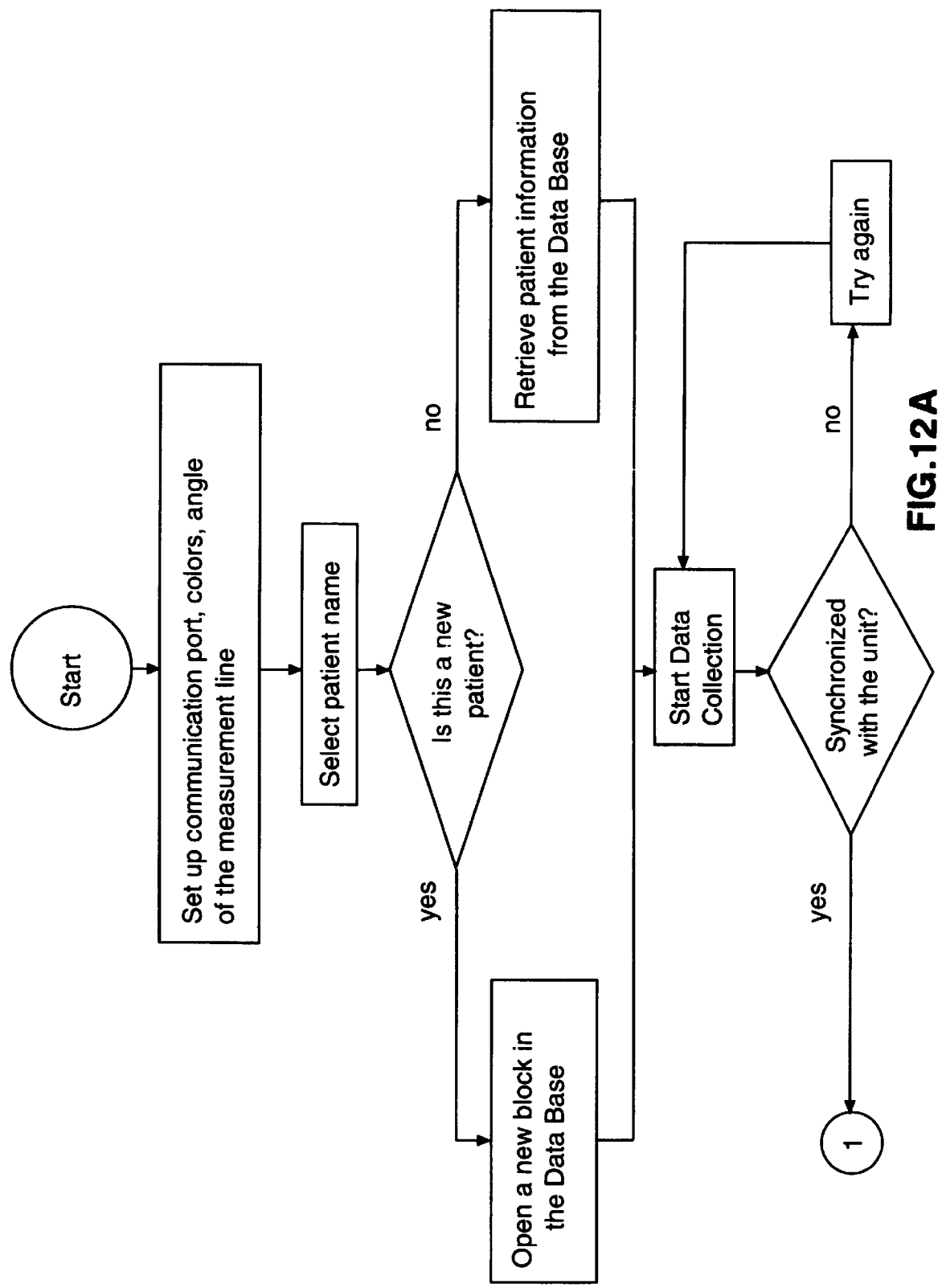
FIG. 12 is a flowchart of the operation of the apparatus.
Figure 12B:
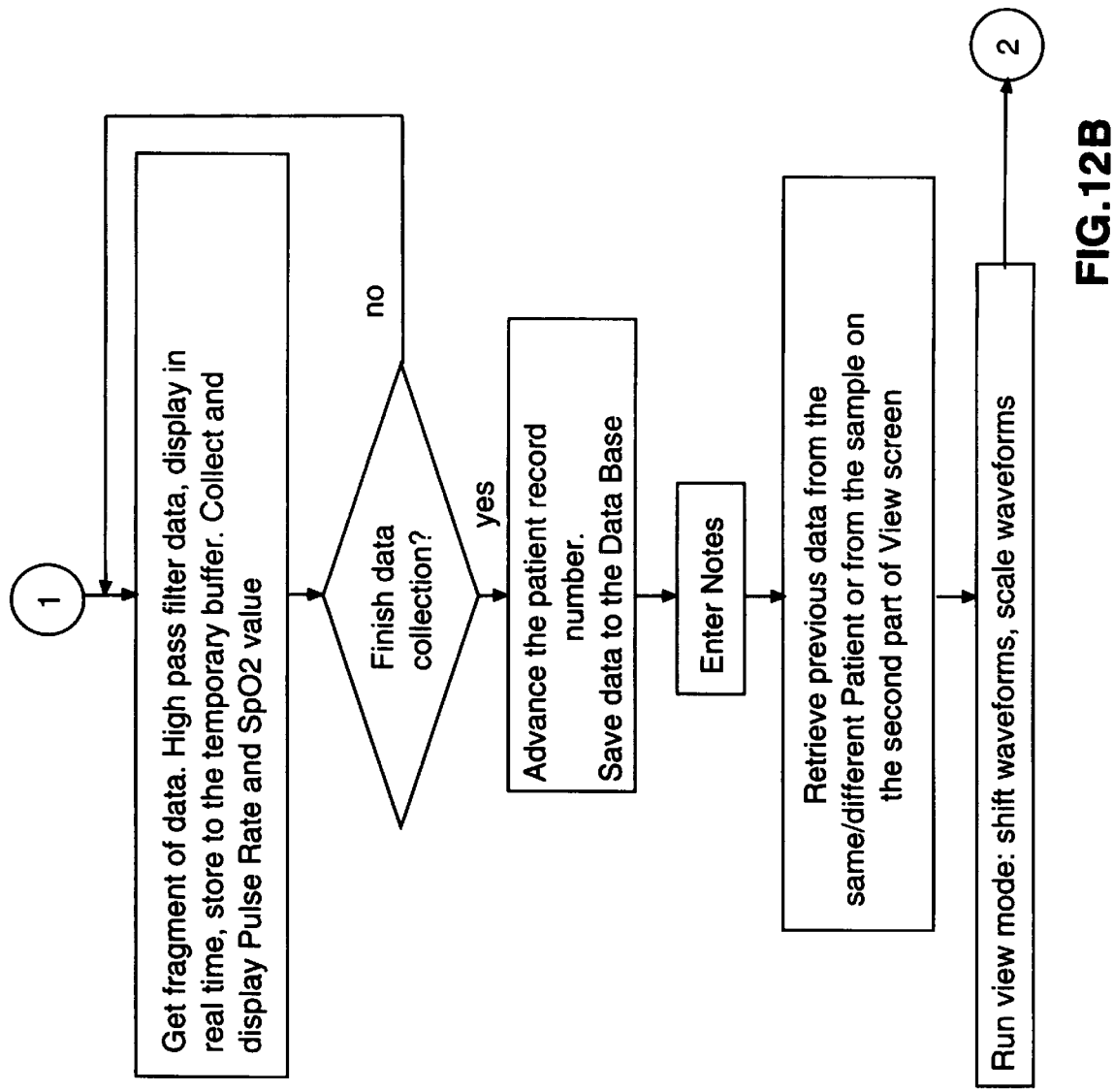

A flow chart of the operation of the apparatus is shown in FIGS. 12a, 12b and 12c. An initial set-up routine sets up the apparatus according to parameters selected by the user. These parameters include the communications, display and analysis parameters (such as ATP ramp angle).

The name of the patient is keyed into the apparatus for data storage purposes. If the patient is a new patient a new database is opened. If the program detects the name of an existing patient the historical data for that patient is retrieved.

Once the equipment is set-up and the patient information is entered, data collection is commenced. A sub-routine checks synchronisation between the oximeter and the processing means. If the units are not synchronised or synchronicity is lost, the data collection process is recommenced.

The collected data is high pass filtered, displayed on the display means in real time and stored in a temporary buffer. The pulse rate and $SpO_2$ values are read from the oximeter interface and displayed. Data collection continues for a timed period or until terminated by the operator.

Upon completion of data collection the patient record number is advanced by one and the data is saved to the patient data base. Notes can be entered by the operator if desired.

Comparative data is then retrieved and displayed on the display means with the recorded data. The comparative data may be previous data from the same or a different patient or may be standard data from a compiled library. The operator is able to make a number of comparisons between the new recorded data and the other data on screen. The waveforms can be shifted or scaled as desired.

The patient records or patient data can be deleted or renamed if required. Certain fragments of the waveforms can be zoomed for calculation of indicative diagnostic values. Indicative diagnostic ratios include the heart activity or time ratio and the amplitude ratio.

The ATP ramp line may be drawn by using a mouse or cursor keys to move a cursor to the start of an ATP ramp. The line is drawn at an angle provided at set-up.

A printer interface is provided in the software so that the waveforms and notes may be printed as required. Help files are also provided to assist users of the apparatus. The help files provide details of operating procedures as well as descriptions of common waveforms.

Figure 13:
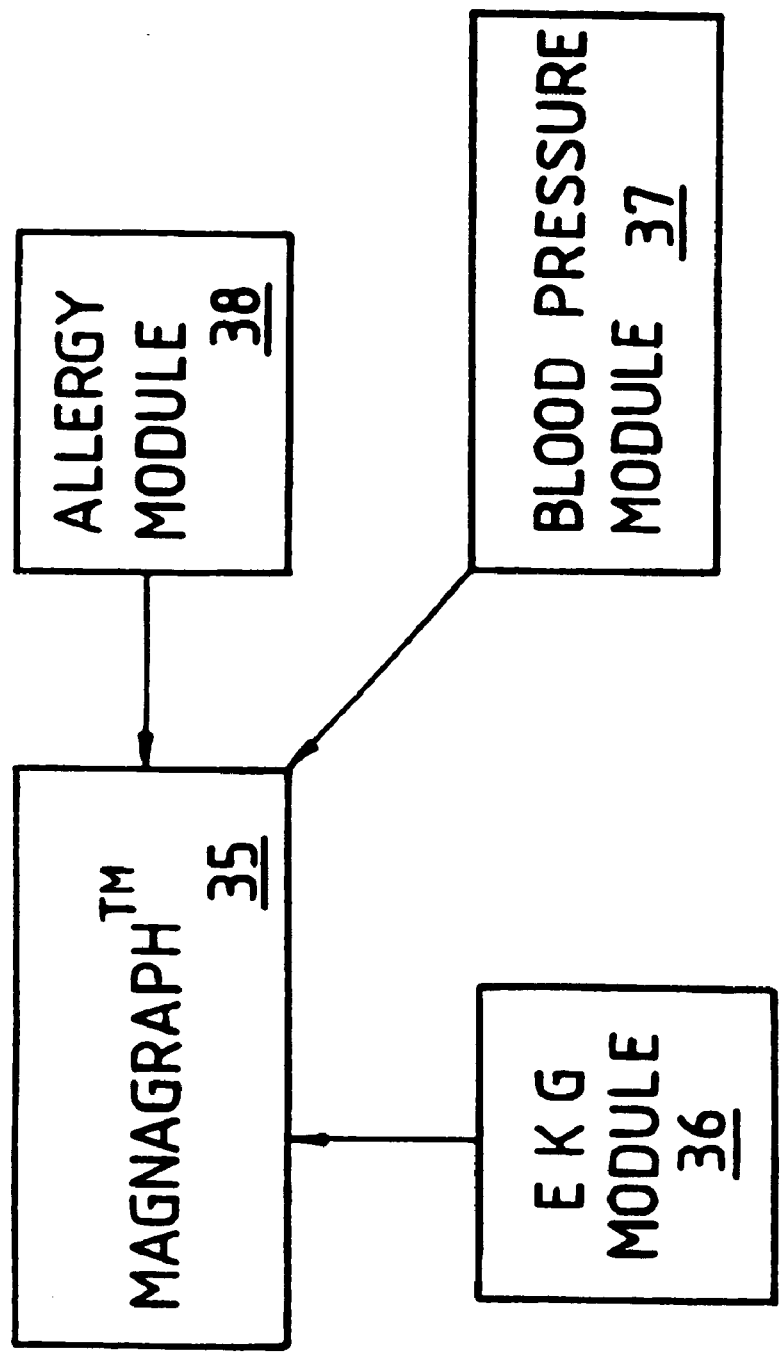
FIG. 13 is a block diagram of additional modules for the apparatus.

The apparatus may incorporate additional modules to extend the data collection functions to include a diagnostic capability. FIG. 13 is a schematic of the modular nature of the invention. The primary module, as described in detail above, is known by the inventors as the Magnagraph™ 35. An EKG Module 36 may interface to the Magnagraph™ 35 to provide an electrical readout of the heart function which, added to the Magnagraph™ physical and mechanical evaluation, renders a complete and objective profile of the cardiac function. A Pulse Blood Pressure Module 37 provides diastolic, systolic and mean arterial pressure, creating a comprehensive and objective evaluation of the profile of the cardiac function. An Allergy Module 38 provides an objective computer based evaluation and assessment of electrodermal readings of known allergens by registering before and after microvoltage changes in response to allergens.

Previously, the allergen response described earlier could only be interpreted subjectively. The Allergy Module 38 provides objective evaluation by comparing measured waveforms with a library of known responses.

It will be appreciated that the apparatus and method described herein are useful for collecting and displaying bioenergetic data collected from a body. Although the description has been in terms of application to a human body it may equally be applied to animals. It will be further appreciated that the collected data can be analysed to varying degrees to provide information of greater value to a medical practitioner or veterinarian. It should be emphasised that the invention is not a prognostic device but only provides data for further consideration by an appropriately skilled practitioner.

The preferred embodiments described herein are intended to illustrate the principles of the invention, but not to limit its scope. Other embodiments and variations to the preferred embodiments may be evident to those skilled in the art and may be made without departing from the spirit and scope of the invention.

What is claimed is:

1. An apparatus for the collection of bioenergetic data indicative of bioenergetic status of a body comprising:
   a) optical monitoring means comprising detection means adapted to detect light and one or more light sources, the optical monitoring means being arranged and configured such that in use light from the one or more light sources passes through a part of the body of a patient, whereby the light is affected by the light characteristics of the part of the body and modulated by blood flowing within the part of the body, the optical monitoring means producing time-varying signals in response to the light detected by the detection means;
   b) display means for displaying a trace;
   c) processing means in signal connection with the optical monitoring means and the display means for processing the time-varying signals and for effecting display of the trace on the display means; and
   d) wherein:
      i) the optical monitoring means produce time-varying signals including high frequency components of the detected light, wherein said high frequency components are above the fundamental systolic pulse and diastolic pulse frequencies;
      ii) the trace is derived from the time-varying signals, whereby the trace displays the high frequency components in the time-varying signals; and
      iii) the high frequency components are indicative of bioenergetic data.

2. The apparatus of claim 1, further comprising an isolation means in signal connection with the optical monitoring means and the processing means, the isolation means providing electrical isolation between the monitoring means and the processing means.

3. The apparatus of claim 1, wherein the detection means is a photodiode, the photodiode producing the time-varying signals and being responsive to light received from said one or more light sources.

4. The apparatus of claim 1, wherein the optical monitoring detector comprises interface means, wherein the interface means performs preliminary processing of the time-varying signals from the detection means including converting analogue signals from the detection means to digital signals suitable for processing by the processing means.

5. The apparatus of claim 1, wherein the processing means is a microprocessor programmed to perform one or more algorithms to calculate bioenergetic data from the time-varying signals and to analyse the bioenergetic data to indicate bioenergetic status.

6. The apparatus of claim 1, wherein the bioenergetic data includes one or more measurable characteristics chosen from a list including: ATP ramp angle, heart activity to rest ration, systolic pulse amplitude variation over time, systolic pulse amplitude to diastolic pulse amplitude ratio, and pulse shape variation.

7. The apparatus of claim 1, wherein the bioenergetic status of the body is indicated according to indicative functions chosen from a list including: pulse rate, oxygen saturation in terminal tissue blood flow rate, elasticity of blood vessels, strength and regularity of heart beat, cardiac sufficiency, cardiac valve activity, cardiac or vascular metabolic abnormalities, cell energy change, latent hypertension, myocardium damage, cardiac inflammation, vascular inflammation, allergic response, immune system response changes, pulmonary function variation, cardiac function variation, intestinal bioenergetic reactions by analysis of the time-varying signals in conjunction with the bioenergetic data.

8. The apparatus of claim 1, wherein the display means is a high resolution video display adapted to display graphical and alphanumeric data.

9. The apparatus of claim 1, further comprising an allergy module in signal connection with the processing means, the allergy module comprising recording means adapted to record electrodermal readings in the form of before and after microvoltage changes occurring in response to known allergens, and analysis means adapted to provide signals characteristic of allergic reaction to known allergens by analysing said electrodermal readings and performing an objective computer based evaluation and assessment, wherein the processing means analyses the bioenergetic data and the signals characteristic of allergic reaction to indicate bioenergetic status.

10. The apparatus of claim 1, further comprising an EKG module in signal connection with the processing means, the EKG module adapted to produce signals characteristic of heart function, wherein the processing means analyses the bioenergetic data and the signals characteristic of heart function to indicate bioenergetic status.

11. The apparatus of claim 1, further comprising a pulse blood pressure module in signal connection with the processing means, the pulse blood pressure module adapted to provide signals characteristic of pulse pressure including diastolic, systolic and mean arterial pressure, wherein the processing means analyses the bioenergetic data and the signals characteristic of pulse pressure to indicate bioenergetic status.

12. An apparatus for the collection of bioenergetic data indicative of bioenergetic status of a body comprising:
 a) optical monitoring means producing time-varying signals in response to light detected by detection means, wherein said light has passed through and been affected by the light characteristics of a part of the body and modulated by blood flowing within the part of the body, wherein the time-varying signals include high frequency components of the detected light and wherein the high frequency components are above the fundamental systolic pulse and diastolic pulse frequencies;
 b) display means for displaying a trace;
 c) processing means in signal communication with the optical monitoring means and the display means for processing the time-varying signals and for effecting display of the trace on the display means;
 d) wherein:
  i) the trace is derived from the time-varying signals;
  ii) the display means are suitable for displaying the high frequency components in the time-varying signals;
  iii) the high frequency components are indicative of bioenergetic data;
  iv) the processing means extract bioenergetic data from the time-varying signals and determine bioenergetic status from the bioenergetic data,
  v) the processing means analyses the time-varying signals to extract bioenergetic data including one or more of ATP ramp angle, heart activity to rest ration, systolic pulse amplitude variation over time, systolic pulse amplitude to diastolic pulse amplitude ratio, and pulse shape variation; and
  vi) the apparatus facilitates determination of bioenergetic status of a body including one or more of pulse rate, oxygen saturation in terminal tissue blood flow rate, elasticity of blood vessels, strength and regularity of heart beat, cardiac sufficiency, cardiac valve activity, cardiac or vascular metabolic abnormalities, cell energy change, latent hypertension, myocardium damage, cardiac inflammation, vascular inflammation, allergic response, immune system response changes, pulmonary function variation, cardiac function variation, intestinal bioenergetic reactions by analysis of the time-varying signals in conjunction with the bioenergetic data.

13. A method of determining bioenergetic status of a body including the steps of:
 transmitting visible and infrared radiation into terminal tissue;
 measuring a time-varying signal proportional to visible and infrared radiation transmitted through the terminal tissue, wherein the time-varying signal includes high-frequency components of the measured radiation, and wherein the high frequency components are above the fundamental systolic pulse and diastolic pulse frequencies;
 converting the time-varying signal to a digital signal;
 passing the digital signal to a processing means;
 processing the digital signal in the processing means to produce a displayable trace;
 analysing the digital signal to obtain bioenergetic data;
 displaying the displayable trace and bioenergetic data on a display means; and
 analysing the trace and bioenergetic data to determine bioenergetic status.

14. The method of claim 13 further including the step of analysing the time varying signals to provide indicative measures of bioenergetic status.

\* \* \* \* \*